(12) United States Patent
Yassinzadeh

(10) Patent No.: US 9,017,374 B2
(45) Date of Patent: Apr. 28, 2015

(54) DEVICE AND METHOD FOR SEALING BLOOD VESSELS

(75) Inventor: Zia Yassinzadeh, San Jose, CA (US)

(73) Assignee: Cardiva Medical, Inc., Sunnyvale, CA (US)

( * ) Notice: Subject to any disclaimer, the term of this patent is extended or adjusted under 35 U.S.C. 154(b) by 1750 days.

(21) Appl. No.: 10/821,633

(22) Filed: Apr. 9, 2004

(65) Prior Publication Data

US 2005/0228443 A1 Oct. 13, 2005

(51) Int. Cl.
*A61B 17/08* (2006.01)
*A61B 17/00* (2006.01)
*A61B 17/22* (2006.01)

(52) U.S. Cl.
CPC ... *A61B 17/0057* (2013.01); *A61B 2017/00672* (2013.01); *A61B 2017/22065* (2013.01)

(58) Field of Classification Search
CPC ............ A61B 17/0057; A61B 2017/00637; A61B 2017/00557; A61B 2017/00672; A61B 2017/22065; A61M 5/16881
USPC .......................................... 606/213–215, 191
See application file for complete search history.

(56) References Cited

U.S. PATENT DOCUMENTS

| | | |
|---|---|---|
| 4,744,364 A | 5/1988 | Kensey |
| 4,852,568 A | 8/1989 | Kensey |
| 4,890,612 A | 1/1990 | Kensey |
| 5,061,274 A | 10/1991 | Kensey |
| 5,108,421 A | 4/1992 | Fowler |
| 5,171,259 A | 12/1992 | Inoue |
| 5,197,971 A | 3/1993 | Bonutti |
| 5,258,000 A | 11/1993 | Gianturco |
| 5,290,552 A | 3/1994 | Sierra et al. |
| 5,292,332 A | 3/1994 | Lee |
| 5,383,896 A | 1/1995 | Gershony et al. |
| 5,419,765 A | 5/1995 | Weldon et al. |

(Continued)

FOREIGN PATENT DOCUMENTS

| | | |
|---|---|---|
| JP | 2000-507838 T | 6/2000 |
| WO | WO 92/22252 | 12/1992 |

(Continued)

OTHER PUBLICATIONS

U.S. Appl. No. 10/718,504, filed Nov. 19, 2003.

(Continued)

*Primary Examiner* — Elizabeth Houston
*Assistant Examiner* — Son Dang
(74) *Attorney, Agent, or Firm* — Wilson Sonsini Goodrich & Rosati

(57) ABSTRACT

The present invention provides devices, systems, and methods for percutaneously sealing a puncture site in tissue tracts and vessels in human or animal bodies. One system includes a locating assembly that is used to locate the puncture site and can also provide temporary hemostasis when the system is used for closing a vessel puncture. The system also includes a compression assembly comprising a tubular member with a balloon on a distal end thereof. This balloon is at a fixed distance from the locator tip which locates the balloon outside the vessel wall at a predetermined distance. Inflation of this balloon causes forward elongation of the balloon which compresses subcutaneous tissue between the distal tip of the balloon and the vessel wall. This tissue compression against the puncture site is the mechanism that provides hemostasis.

14 Claims, 16 Drawing Sheets

(56) References Cited

U.S. PATENT DOCUMENTS

| | | | |
|---|---|---|---|
| 5,454,833 A | 10/1995 | Boussignac et al. | |
| 5,456,667 A | 10/1995 | Ham et al. | |
| 5,486,195 A * | 1/1996 | Myers et al. | 606/213 |
| 5,507,744 A | 4/1996 | Tay et al. | |
| 5,626,601 A | 5/1997 | Gershony et al. | |
| 5,630,833 A | 5/1997 | Katsaros et al. | |
| 5,634,936 A | 6/1997 | Linden et al. | |
| 5,645,566 A | 7/1997 | Brenneman et al. | |
| 5,728,134 A * | 3/1998 | Barak | 606/214 |
| 5,782,860 A | 7/1998 | Epstein et al. | |
| 5,810,810 A | 9/1998 | Tay et al. | |
| 5,851,210 A | 12/1998 | Torossian | |
| 5,861,003 A | 1/1999 | Latson et al. | |
| 5,868,778 A | 2/1999 | Gershony et al. | |
| 5,895,398 A | 4/1999 | Wensel et al. | |
| 5,922,009 A | 7/1999 | Epstein et al. | |
| 5,951,583 A | 9/1999 | Jensen et al. | |
| 5,957,952 A | 9/1999 | Gershony et al. | |
| 6,012,457 A | 1/2000 | Lesh | |
| 6,017,359 A | 1/2000 | Gershony et al. | |
| 6,048,358 A | 4/2000 | Barak | |
| 6,056,770 A | 5/2000 | Epstein et al. | |
| 6,071,300 A | 6/2000 | Brenneman et al. | |
| 6,080,182 A | 6/2000 | Shaw et al. | |
| 6,146,396 A | 11/2000 | Konya et al. | |
| 6,248,124 B1 | 6/2001 | Pedros et al. | |
| 6,296,657 B1 | 10/2001 | Brucker | |
| 6,464,712 B1 | 10/2002 | Epstein et al. | |
| 6,656,207 B2 | 12/2003 | Taylor et al. | |
| 6,913,614 B2 | 7/2005 | Marino et al. | |
| 7,025,776 B1 | 4/2006 | Houser et al. | |
| 7,115,127 B2 | 10/2006 | Lindenbaum et al. | |
| 7,223,266 B2 | 5/2007 | Lindenbaum et al. | |
| 7,621,936 B2 * | 11/2009 | Cragg et al. | 606/213 |
| 2002/0072767 A1 | 6/2002 | Zhu | |
| 2002/0133123 A1 | 9/2002 | Zucker | |
| 2002/0156495 A1 * | 10/2002 | Brenneman et al. | 606/213 |
| 2002/0165581 A1 * | 11/2002 | Brucker | 606/213 |
| 2003/0055454 A1 * | 3/2003 | Zucker | 606/213 |
| 2003/0191493 A1 | 10/2003 | Epstein et al. | |

FOREIGN PATENT DOCUMENTS

| | | |
|---|---|---|
| WO | WO 95/05121 | 2/1995 |
| WO | WO 96/24290 | 8/1996 |
| WO | WO 98/34546 | 8/1998 |
| WO | WO 98/40017 | 9/1998 |
| WO | WO 00/06029 | 2/2000 |
| WO | WO 00/06031 | 2/2000 |

OTHER PUBLICATIONS

Datascope Corporation; "VasoSeal" product brochure; 1991.
Sherwood, Davies & Geck; "AngioSeal" product brochure; 1977.
Office Action of Japanese Patent Application No. 2007-507469, mailed Dec. 13, 2010, 3 pages total. [No English Translation].

* cited by examiner

DEVICE AND METHOD FOR SEALING BLOOD VESSELS

BACKGROUND OF THE INVENTION

1. Field of the Invention

The present invention relates generally to devices, systems, and methods for percutaneous sealing of a puncture site in tissue tracts. More specifically, the present invention relates to devices, systems, and methods for hemostasis of vascular puncture sites in human bodies.

Percutaneous access of blood vessels in the human body is routinely performed for diagnostics or interventional procedures such as coronary and peripheral angiography, angioplasty, atherectomies, placement of vascular stents, coronary retroperfusion and retroinfusion, cerebral angiograms, treatment of strokes, cerebral aneurysms, and the like. Patients undergoing these procedures are often treated with anti-coagulants such as heparin, thrombolytics, and the like, which make the closure and hemostasis process of the puncture site in the vessel wall at the completion of such interventional procedures more difficult to achieve.

Various devices have been introduced to provide hemostasis, however none have been entirely successful. Some devices utilize collagen or other biological plugs to seal the puncture site. Alternatively, sutures and/or staples have also been applied to close the puncture site. External foreign objects such as plugs, sutures, or staples however may cause tissue reaction, inflammation, and/or infection as they all "leave something behind" to achieve hemostasis.

There is also another class of devices that use the body's own natural mechanism to achieve hemostasis wherein no foreign objects are left behind. Such devices typically provide hemostasis by sealing the puncture site from the inside of the vessel wall wherein the device is left in place in the vessel lumen until hemostasis is reached and thereafter removed. Although such devices have achieved relative levels of success, removal of the device at times may disrupt the coagulant that is formed at the puncture site. This in turn may cause residual bleeding which requires the device user to apply a few minutes of external manual pressure at the puncture site after the removal of the device to achieve complete hemostasis.

Still further devices that also uses body's natural mechanism to achieve hemostasis comprise a locator on the inside of the vessel wall and a balloon to directly contact and seal the puncture site from the outside surface of the vessel wall. This balloon is directly against and in contact with the outside surface of the vessel wall for sealing the hole and achieving hemostasis. There are several drawbacks associated with direct contact and compression of the outside surface of the vessel wall. For example, excessive compression may cause herniation of the balloon through the puncture site into the vessel, which in turn may cause resumption of bleeding. Further, such devices may not be easily applied to severely tortuous vessels where direct access and contact with the vessel surface to seal the puncture may be difficult to achieve. Moreover, such devices may substantially disrupt the flow of blood in the vessel during its application. Further, intimate device contact with the puncture site of the vessel wall may not provide sufficient coagulant. Still further, removal of the device may cause disruption of the coagulant at the puncture site thereby increasing the chances for resumption of bleeding and hematoma formation (i.e., leaking of blood into interstitial space).

In light of the above, it would be desirable to provide improved devices, systems, and methods for complete hemostasis of a puncture site in a body lumen, particularly blood vessels of the human body. It would be particularly desirable if such devices, systems, and methods utilized the body's own natural healing mechanism to achieve hemostasis without disrupting coagulation formation at the puncture site. It would be further desirable if such devices, systems, and methods prevented any vessel herniation or vessel flow disruption. Further, such devices, systems, and methods should be easy to implement on a variety of vessel anatomies. At least some of theses objectives will be met by the devices, systems, and methods of the present invention described hereinafter.

2. Description of the Background Art

Expansible devices for use in blood vessels and tracts in the body are described in co-pending U.S. patent application Ser. No. 10/718,504, assigned to the assignee of the present application. The following U.S. patents and publications may be relevant to the present invention: U.S. Pat. Nos. 4,744,364; 4,852,568; 4,890,612; 5,108,421; 5,171,259; 5,258,000; 5,383,896; 5,419,765; 5,454,833; 5,626,601; 5,630,833; 5,634,936; 5,728,134; 5,861,003; 5,868,778; 5,951,583; 5,957,952; 6,017,359; 6,048,358; 6,296,657; U.S. Publication Nos. 2002/0133123 and 2003/0055454.

The full disclosures of each of the above mentioned references are incorporated herein by reference.

BRIEF SUMMARY OF THE INVENTION

The present invention provides improved devices, systems, and methods for complete hemostasis of a puncture site in a body lumen, particularly blood vessels of the human body. Such closure devices, systems, and methods utilize the body's own natural healing mechanism to achieve hemostasis without leaving any foreign objects behind. The devices of the present invention allow for enhanced coagulant formation at the puncture site, increasing the integrity of hemostasis. Further, removal of such sealing devices and systems after hemostasis is achieved does not incite disruption of the coagulation formation at the puncture site. This in turn reduces the risk of bleeding and hematoma formation, thrombosis, embolization, and infection. The devices, systems, and methods of the present invention substantially avoid dangers of vessel herniation or vessel flow disruption, particularly in lower extremities. Further, such devices, systems, and methods are easy to implement without numerous intermediary steps on a variety of vessel anatomies, such as severely tortuous vessels.

In a first aspect of the present invention, a system for hemostasis of a puncture site in a body lumen is provided. One system comprises a locating assembly and a compression assembly. The locating assembly generally comprises a first tubular member having a proximal end and a distal end and an expansible member disposed on the distal end of the first tubular member. The compression assembly is at least partially coaxial with the locating assembly. The compression assembly comprises a second tubular member having a proximal end and a distal end and a balloon disposed at the distal end of the second tubular member. In particular, a distal end of the balloon is positionable at a predetermined distance away from a wall of the body lumen. An inflation assembly is also provided. It is coupleable to a proximal end of the compression assembly and in communication with the balloon.

Hence, the present invention is designed such that the compression balloon is deployed outside the vessel wall at a predetermined distance from the outside surface of the vessel wall. The balloon, during inflation, compresses the subcutaneous tissue between the vessel wall and the distal surface of the balloon. The compressed tissue can then overcome the blood pressure and hence stop blood from flowing out to achieve hemostasis. It will be appreciated that the balloon is not used as means to directly contact and seal the hole in the vessel wall. Rather, the present invention uses the tissue as the compression medium against the puncture site to achieve hemostasis. The tissue left between the balloon and the vessel wall allows for enhanced coagulation in the vicinity of the puncture site. This allows for more secure hemostasis with reduced chances of delayed bleeding.

The locating assembly further comprises deployment means coupleable to the proximal end of the first tubular member so as to move the expansible member between a contracted configuration and an expanded configuration. The expansible member in the expanded configuration typically has a diameter in a range from about 0.05 inch to about 0.5 inch, preferably in a range from about 0.15 inch to about 0.30 inch. The expansible member generally comprises stainless steel, shape memory material, superelastic material or like medical grade material. The locating assembly may further comprise a temporary hemostasis member, such as a plug, coupleable to the distal end of the first tubular member. In some embodiments, the compression balloon may be disposed between the distal end of the second tubular member and a proximal end of the temporary hemostasis member so as to form an integrated, unitary assembly. In other embodiments, it is preferable that the balloon is disposed solely on the distal end of the compression assembly, as described in more detail below. In still other embodiments, the locating assembly may further comprise a deformable membrane at least partially disposed over the expansible member in lieu or in addition to the temporary hemostasis plug.

Generally, the compression balloon remains proximal a distal end of the expansible member. This predetermined positioning may be implemented in any number of ways. For example, mechanical or visual means on the locating or compression assembly like detents, latches, flanges, other mechanical interference, visual markings, and like mechanisms, may provide positioning of the compression balloon at a fixed distance from the expansible member which locates the balloon outside the vessel wall at the predetermined distance. The predetermined distance of the distal end of the compression balloon from the vessel wall is in a range from about 0.05 inch to about 0.5 inch, preferably in a range from about 0.2 inch to about 0.3 inch. The compression assembly may be fixed relative to the locating assembly. Alternatively, the compression assembly may be moveable relative to the locating assembly. In some instances, the locating assembly may be laterally offset from an axis of the compression assembly. As discussed above, the locating assembly and compression assembly may also form an integrated catheter assembly structure for ease of operation.

The compression balloon may comprise one or more materials selected from the group consisting of polyethylene, polyethylene terephthalate, polytetrafluroethylene, nylon, polyurethane, silicone, latex, polyvinyl chloride, and thermoplastic elastomer. The compression balloon may be preformed or pre-molded symmetrically or asymmetrically. In some embodiments, the balloon has an expanded configuration comprising a conical shape. In other embodiments, the balloon comprises a plurality of concentric folds that are unfolded in an expanded configuration. In further embodiments, the balloon has an expanded configuration comprising a concave distal end. This last design allows for formation of a concave surface relative to the vessel wall when the balloon is inflated, allowing for more coagulant to form at the puncture site which would likely provide for enhanced hemostasis.

The compression assembly may further comprise a radio-opaque material so that the compression balloon placement may be imaged and viewed via fluoroscopy. In some embodiments, a coating on an outer surface of the balloon may be applied. The coating may comprise electrically conductive material for the delivery of energy, such as radio frequency energy or microwave energy to further promote and accelerate complete hemostasis. The coating may further be designed to deliver ultrasound energy. Alternatively, the coating may comprise clot promoting agents, such as thrombin, or anti-infection agents. In the case of agent release, the balloon may alternatively comprise a semi-permeable membrane, allowing the inflation medium, which may be chosen from clot promoting solutions, to diffuse into the surrounding tissue. The inflation assembly generally comprises a source of at least air, fluid, clot promoting agent, anti-infection agent, radio-opaque medium, or a combination thereof.

In another aspect of the present invention, devices for hemostasis of a puncture site in a body lumen are also provided. One device comprises a first tubular member having a proximal end and a distal end and a second tubular member having a proximal end and a distal end. The second tubular member is at least partially coaxial with the first tubular member so as to define an inflation lumen therebetween. A balloon is disposed at the distal ends of the first and second tubular members and in communication with the inflation lumen. A distal end of the balloon is postionable at a predetermined distance away from a wall of the body lumen. The characteristics of the compression balloon are generally as described above. In an additional embodiment, the balloon may comprise an expansible member and a deformable membrane at least partially disposed over the expansible member as described in greater detail in co-pending U.S. patent application Ser. No. 10/718,504, assigned to the assignee of the present application and incorporated herein by reference.

In yet another aspect of the present invention, methods for hemostasis of a puncture site in a body lumen are also provided. One method comprises providing a compression assembly comprising a tubular member having a proximal end and a distal end and a balloon disposed at the distal end of the tubular member. The compression assembly is inserted through an opening in a skin surface. A distal end of the balloon is positioned at a predetermined distance away from a wall of the body lumen and against subcutaneous tissue. The balloon is inflated to an expanded configuration. This causes forward elongation of the balloon which compresses subcutaneous tissue between the distal tip of the balloon and the vessel wall. This tissue compression against the puncture site is the mechanism that provides hemostasis. As described above, the balloon is only engageable against subcutaneous tissue surrounding the body lumen wall, wherein the body lumen comprises a blood vessel. The predetermined distance may be in a range from about 0.05 inch to about 0.5 inch, preferably in a range from about 0.2 inch to about 0.3 inch. The balloon may be imaged during positioning. Further, radio frequency energy, ultrasound energy, microwave energy, clot promoting agents or anti-infection agents may be delivered to the puncture site.

Since the compression assembly of the present invention is seated against the subcutaneous tissue, and is not in contact with the vessel wall, there is further coagulant formation and less chances of disruption of the coagulant at the puncture site (e.g., arteriotomy site) when the device is removed. It is thus expected that the chances of resumption of bleeding or complications such as formation of hematoma are greatly reduced. Further, since the compression balloon is at a predetermined distance away from the vessel wall and against subcutaneous tissue, the risks of the balloon herniating into the puncture site and into the vessel are greatly reduced.

Moreover, as the compression assembly relies on tissue compression and not intimate and complete seating of the balloon around the periphery of the puncture site to achieve sealing of the hole, it can therefore be applied with less precision and is less dependant on the anatomy of the site. In other words, the compression assembly is more forgiving in its application since it is less reliant on positioning and as such may be even applied to seal severely tortuous vessels. The compression assembly can also be used more reliably and therefore has a greater chance of success.

The proposed design of the balloon and the attachment technique provide for forward movement of the distal end of the balloon towards the vessel wall, causing tissue compression, when inflated. For example, inflating may comprise at least one of axial or radial dilation of the balloon so as to cause targeted micro compression of the subcutaneous tissue surrounding the body lumen wall. Alternatively, inflating may comprise expanding a superior aspect of the balloon greater than an inferior aspect of the balloon. Since the tubular member is often not positioned perpendicularly to the vessel, this embodiment compensates for the difference in the distance between the top distal tip of the balloon to the vessel wall and the bottom distal tip of the balloon to the vessel wall so as to provide for more even compression over the puncture site. Optionally, inflating may comprise expanding a distal face of the balloon at an angle to the tubular member similar to an angle formed between the tubular member and the body lumen. Inflating may also comprise simply deploying the balloon to an expanded configuration comprising a conical shape. Still further, inflating may comprise unfolding concentric folds of the balloon to an expanded configuration or deploying the balloon to an expanded configuration having a concave distal end.

A locating assembly comprising a second tubular member having a proximal end and a distal end and an expansible member disposed on the distal end of the second tubular member is also preferably provided. The locating assembly may be inserted through the opening in the skin and in the puncture site prior to or simultaneously with compression assembly insertion. The expansible member is deployed to an expanded configuration within the body lumen having a diameter in a range from about 0.05 inch to about 0.5 inch. The puncture site in the body lumen wall is then located and temporary hemostasis of the puncture site with a plug coupleable to the distal end of the second tubular member may also be provided. After balloon inflation and initial compression, the locating assembly is contracted and withdrawn from the skin.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

DETAILED DESCRIPTION OF THE INVENTION

Figure 1A:
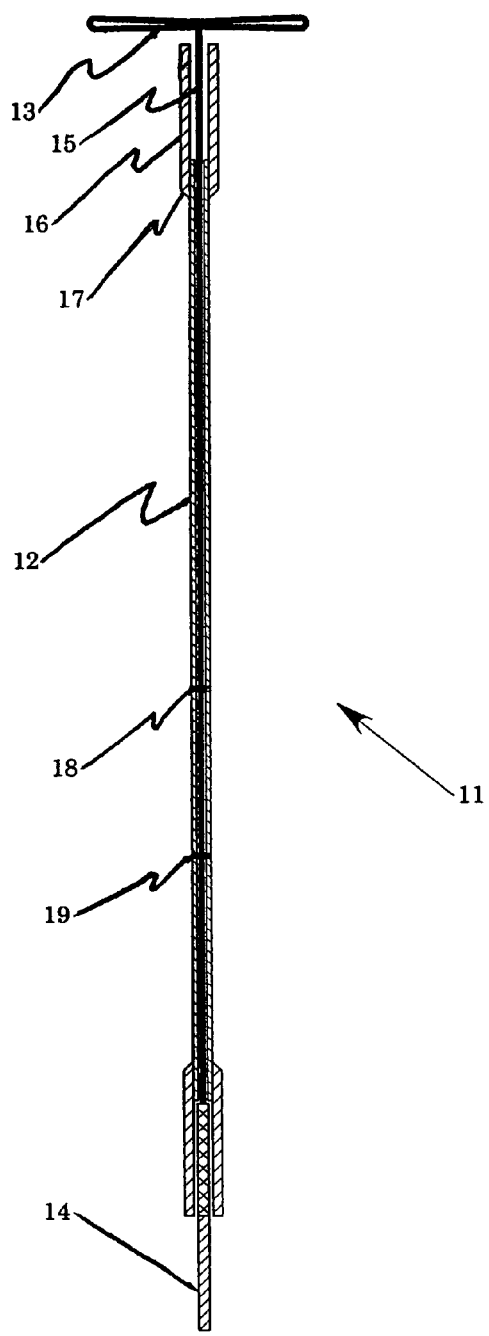
FIGS. 1A and 1B illustrate a locating assembly in an expanded configuration and retracted configuration respectively.
Figure 1B:
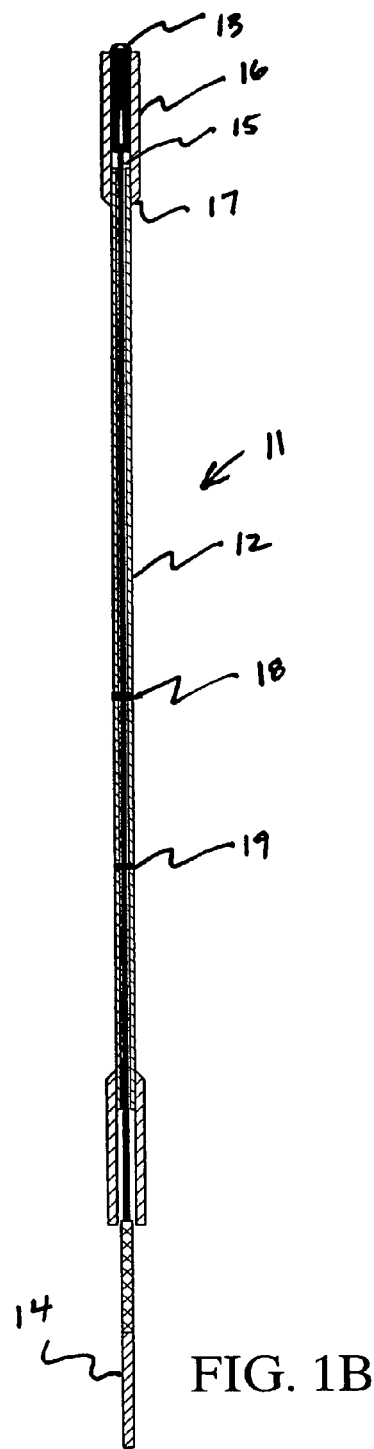
Figure 1C:
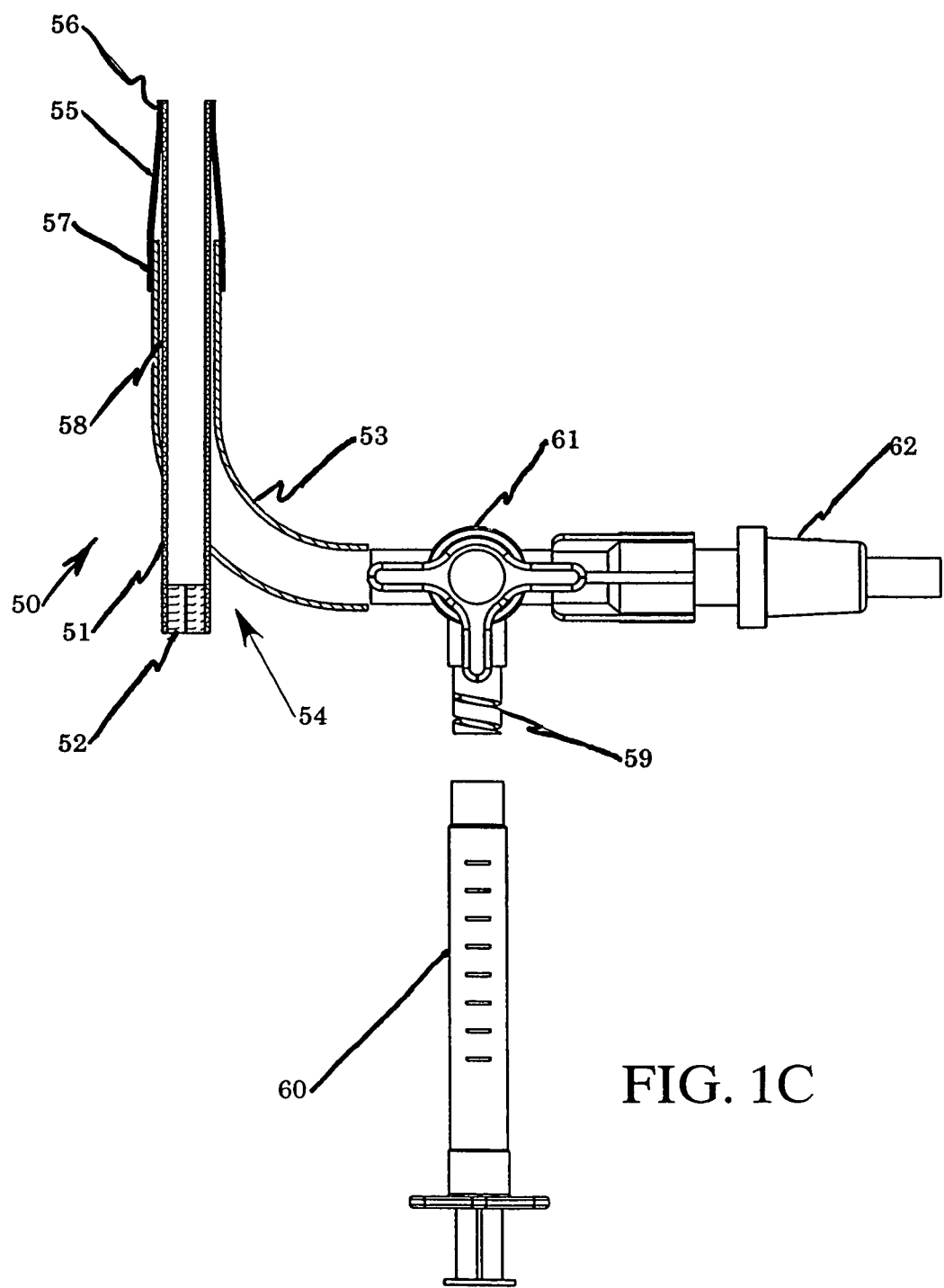
FIG. 1C illustrates a balloon compression assembly in a collapsed configuration.

Referring to FIGS. 1A through 1D, an exemplary embodiment of a system 10 for hemostasis of a puncture site in a body lumen constructed in accordance with the principles of the present invention is illustrated. The system generally comprises a locating/temporary hemostasis assembly 11 as illustrated in FIG. 1A and a compression assembly 50 as illustrated in FIG. 1C. The locating/temporary hemostasis assembly 11 comprises a flexible elongated tubular member 12 and a locating feature 13. The locating feature 13 comprises an expansible member which can move between an expanded state, as shown in FIG. 1A, and a contracted state, as shown in FIG. 1B. A membrane may be present that fully or partially covers this expansible member 13. Deployment means of the expansible member 13 located at a proximal end of the tubular member 12 may comprise a handle 14 and push/pull member 15 combination. The handle assembly 14 at the proximal end can facilitate the movement of the expansible member 13 via the push/pull member 15 which connects the handle assembly 14 to the expansible member 13. This member 15 may be in the form of a wire of sufficient column strength to deploy and retract the expansible member 13. It will be appreciated that the above depictions are for illustrative purposes only and do not necessarily reflect the actual shape, size, or dimensions of the system 10. This applies to all depictions hereinafter.

A distal end of tubular member 12, just proximal to the expansible member 13, is of sufficient diameter to temporarily seal the puncture in the vessel wall. Hemostasis plug 16 temporarily stops bleeding while the compression balloon is being deployed. The temporary hemostasis plug 16 is tapered at a proximal end 17 to facilitate its use and avoid any potential binding. Plug 16 may have a minimum length of 0.05 inch or it may extend the entire length of the tubular member 12. Plug 16 may have a diameter in range from about 0.04 inch to about 0.2 inch. The effectiveness of the plug 16 to achieve temporary hemostasis may depend on a sheath size and the extent of the dilation of the puncture site. In such cases, the assembly 11 may be designed and manufactured to be used in conjunction with a specific size or a range of sheath sizes. Temporary hemostasis plug 16 may then be tailored accordingly. For example, procedures using a 5 to 6 Fr sheaths may have a temporary hemostasis plug that is approximately 0.070 inch in diameter. This diameter is large enough to produce temporary hemostasis yet small enough to go through a 5 Fr sheath. Plug 16 may also fully or partially house the contracted expansible member 13. It is generally desirable to remove the sheath once the closure assembly 11 is applied. Therefore, locating/temporary hemostasis assembly 11 may have a smaller cross-sectional profile than an inside diameter of the sheath used.

Referring now to FIG. 1C, the compression assembly 50 of the hemostasis system 10 includes elongated tubular members 51 and 53 and compression balloon 55. An inner diameter of first tubular member 51 is large enough so that it can preferably accept all, or at least a portion of the locating/temporary hemostasis assembly 11. As shown, a proximal end of compression tubular member 51 is equipped with a sealing mechanism 52 such as a silicone seal. Since compression tubular member 51 may be in fluid communication with blood, seal 52 prevents blood from flowing out of the system 10. Seal 52 may be disposed anywhere along a length of the compression tubular member 51. The length of compression member 51 from the seal 52 to a distal tip thereof is substantially shorter than a length of the locating/temporary hemostasis assembly 11, approximately half the length. Locating assembly 11 may have a length in a range from about 4 inches to about 18 inches, preferably from about 8 inches to about 12 inches. This ensures that the handle assembly 14 of assembly 11 can be pushed through seal 52 when member 11 is positioned in the vessel.

The second flexible tubular member 53 may be concentric with and contain the first tubular member 51. This second tubular member 53 may expand distally the full length of the first tubular member 51. The two tubular members 51 and 53 may bifurcate proximally as depicted by arrow 54. It will be appreciated that these two tubular members 51 and 53 may be fabricated from a multi-lumen tubing using common extrusion processes. In general, all tubular members 12, 51, and 53 may be formed from polyester (e.g., polyethylene terephthalate), PEBAX™, PEEK™, nylon, polyvinyl chloride, and like medical grade materials. A distal end of the compression assembly 50 is equipped with a compression balloon 55 which is attached at a distal end 56 and a proximal end 57 thereof. The balloon 55 is in communication with an inflation lumen 58 that is formed between the two tubular members 51 and 53 of the compression assembly 50. A proximal end of the second tubular member 53 is equipped with a luer lock 59 for attaching a syringe 60 or the like to pump air or fluids, such as saline solution, into compression balloon 55 for the purpose of inflating the balloon. The inflation assembly may also be equipped with a stopcock 61, distal to luer lock 59, that maintains the pressure once the balloon is inflated to its desired pressure. The device may also include a pressure relief valve 62 that automates and visually verifies when the desired pressure of the compression balloon 55 is reached. The pressure relief valve 62 would take the guess work out of the required amount of pressure to be applied to the compression balloon 55.

Figure 1D:
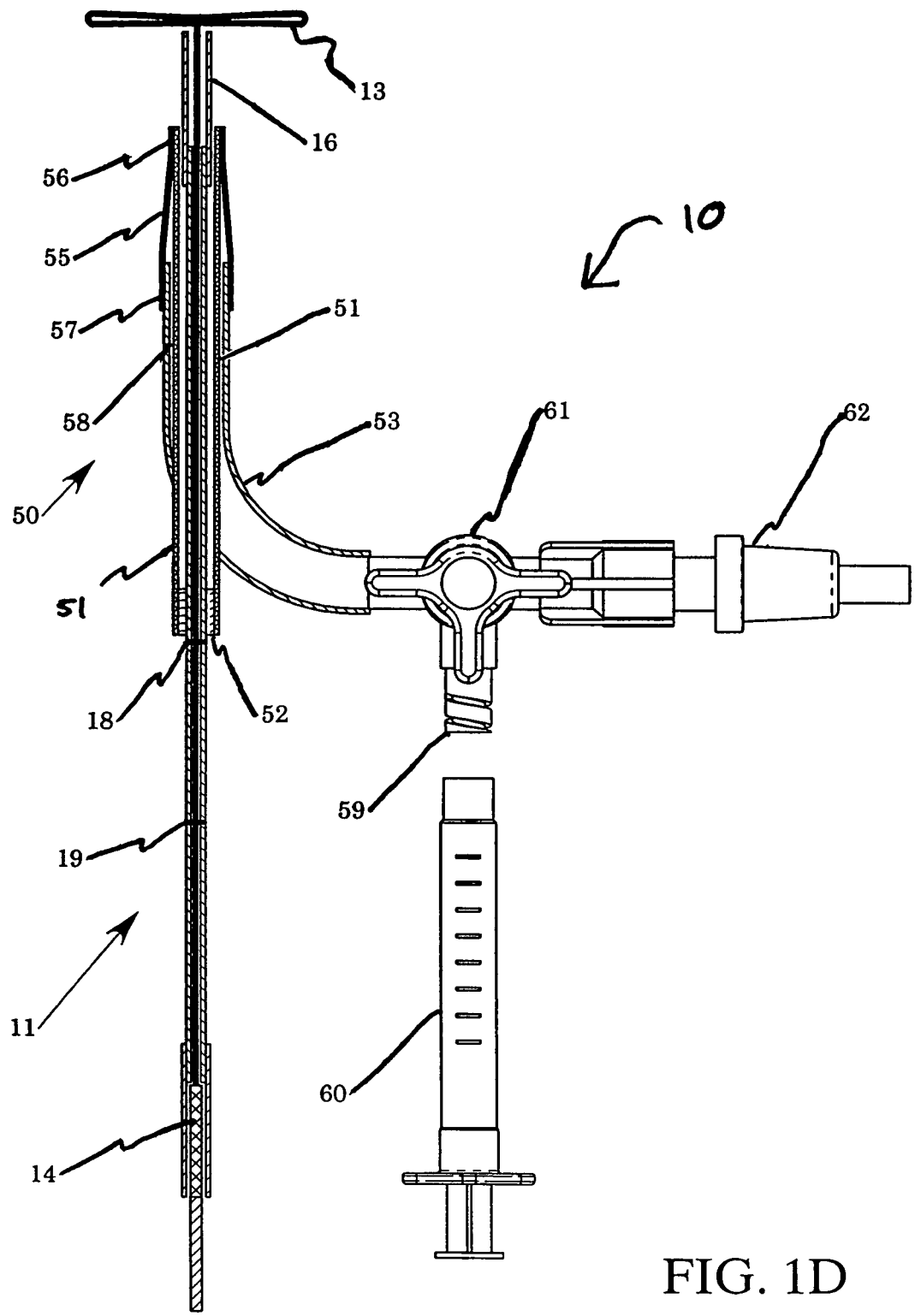
FIG. 1D illustrates a system for hemostasis of a puncture site in a body lumen employing the assemblies of FIGS. 1A-1C constructed in accordance with the principles of the present invention.

Referring now to FIG. 1D, the interaction of assemblies 11 and 50 of the closure system 10 is shown. Locating/temporary hemostasis assembly 11 slides inside compression assembly 50 such that the distal tip 56 of compression balloon 55 gets located at a fixed distance proximal to locating expansible member 13 of assembly 11. The locating process may be achieved by aligning visual marks on the two assemblies, such as aligning mark 18 of locating assembly 11 to be just outside seal 52 of compression assembly 50. Alternatively, the locating process may be achieved as a result of a mechanical interference or a latching mechanism. The latching mechanism may be designed to provide an audio or a tactile feedback when the two tubular assemblies 11 and 50 latch. Once the two assemblies are latched, the latching mechanism can allow assembly 11 to move distally with minimal force. This detent, however, resists further forward movement of compression assembly 50 relative to assembly 11. The distal movement of assembly 11 relative to compression member 50 may be desirable when the compression balloon 55 is inflated. The inflation of the compression balloon 55 may push the vessel wall distally. Having assembly 11 move with minimal force, such as 1 to 20 ounces, preferably 5 to 10 ounces, in the same direction would eliminate exerting stress on the vessel wall.

Figure 2A:
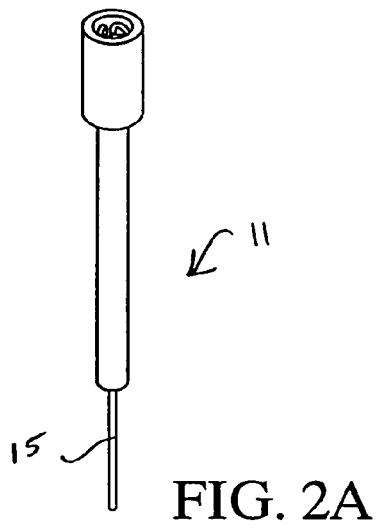
FIGS. 2A and 2B illustrate another embodiment of the locating assembly in a retracted configuration and an expanded configuration respectively that may be employed in any of the systems disclosed herein.
Figure 2B:
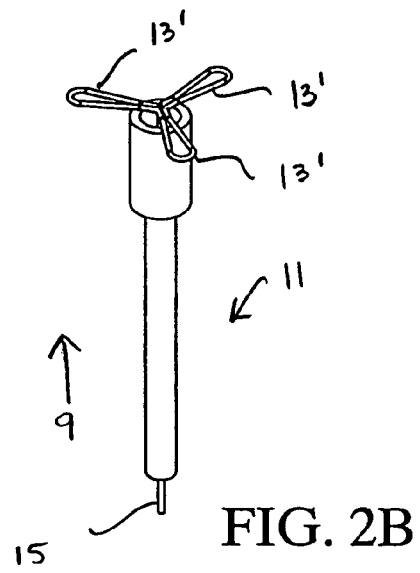
Figure 3A:
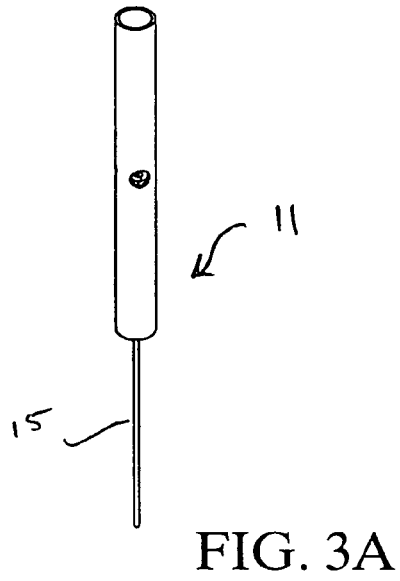
FIGS. 3A and 3B illustrate yet another embodiment of the locating assembly in a retracted configuration and an expanded configuration respectively that may be employed in any of the systems disclosed herein.
Figure 3B:
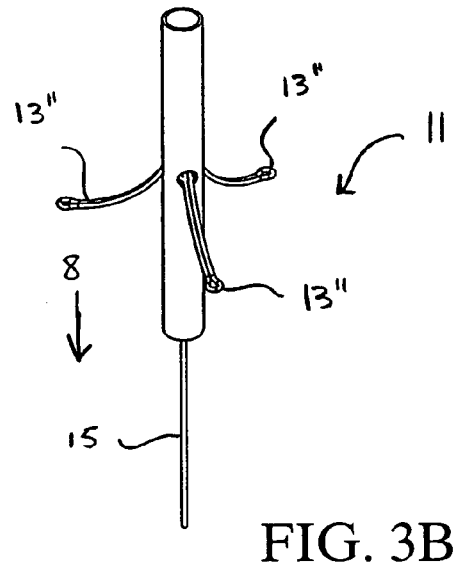

The expansible member 13 of the locating assembly 11 may assume a variety of forms. Some are deployed by pushing the deployment means 15 forwardly. FIGS. 2A and 2B show an example of such a push type expansible member 13' in contracted and deployed states, respectively. In particular, push/pull member 15 is pushed distally as depicted by arrow 9 to deploy fan-like expansible member 13'. Others may have the deployment means 15 connected to a distal end of the expansible member 13" and to deploy the expansible member 13" the deployment means is pulled back. FIGS. 3A and 3B illustrate an example of a pull type expansible member 13" in contracted and deployed states, respectively. In particular, push/pull member 15 is pulled proximally as depicted by arrow 8 to deploy hooks or prongs 13'".

The deployed expansible member 13 produces a cross-sectional diameter that is substantially large so that when the assembly 11 is pulled back in the vessel and the expansible member is seated against the vessel wall, it can produce substantial resistance to the movement of the expansible member and therefore locate the assembly 11 against the puncture site inside the vessel lumen. The expansible member 13, in deployed state, may produce a feature that is in a range from about 0.05 inch to about 0.5 inch in diameter, preferably from about 0.15 inch to about 0.30 inch. The expansible member 13 may be made from suitable metals such as stainless steel, shape memory material, superelastic material (e.g., NITINOL™ wire), etc. which can be elongated, contracted, or constrained without permanent deformation, but at body temperature, when freed or unconstrained returns to the expanded configuration.

Figure 4A:
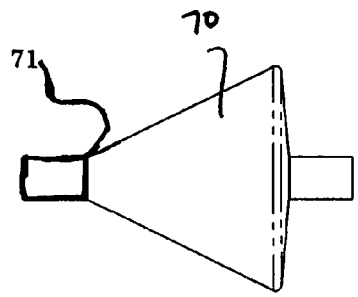
FIGS. 4A and 4B illustrate another embodiment of the balloon that may be employed in any of the compression assemblies disclosed herein.

Compression balloon 55 is designed to perform various functions and exhibit particular behavior, specifically in the case of pre-formed or pre-molded balloons. For example, the proximal end 57 of the balloon 55 may be made in a conical form. FIG. 4A illustrates an example of a simple conical shaped compression balloon 70. During inflation of the balloon 70 the portion closer to the apex 71 inflates to its maximum diameter first, and then inflation is propagated distally. This inflation process may aid in stabilizing the balloon 70 in the tissue and prevents lateral displacement of the compression assembly 50.

Figure 5A:
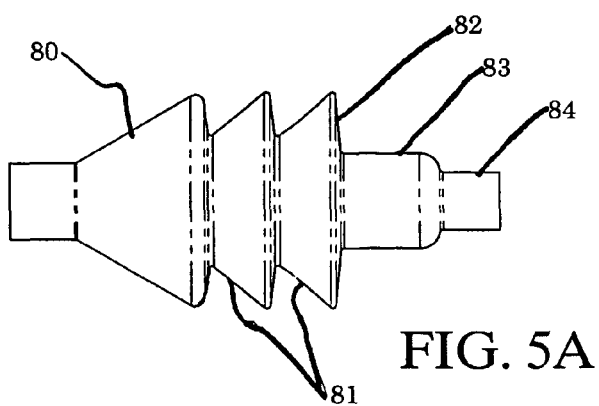
FIGS. 5A through 5C illustrate yet another embodiment of the balloon that may be employed in any of the compression assemblies disclosed herein.
Figure 5B:
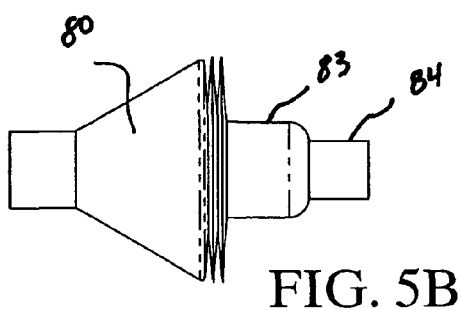
Figure 5C:
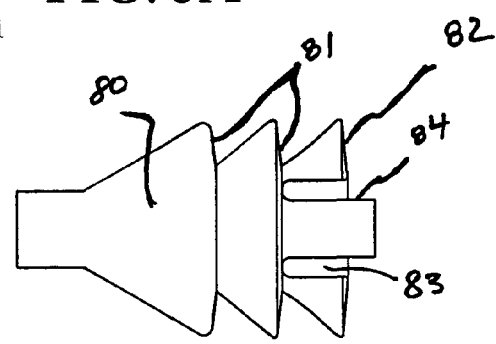

Referring now to FIG. 5A, the balloon may alternatively comprise a plurality of concentric folds that would be unfolded when pressurized. FIG. SA illustrates a compression balloon 80 prior to assembly attachment. Balloon 80 incorporates a plurality of folds 81. The process of unfolding causes the distal end 82 of the balloon to move forward, compressing the tissue in front of the balloon against the puncture site. Feature 83, just proximal to the balloon attachment area 84, folds over the attachment point as the balloon unfolds forwardly to allow for balloon elongation. FIGS. 5B and 5C illustrate the attached balloon 80 prior to inflation and after inflation, respectively.

Figure 6A:
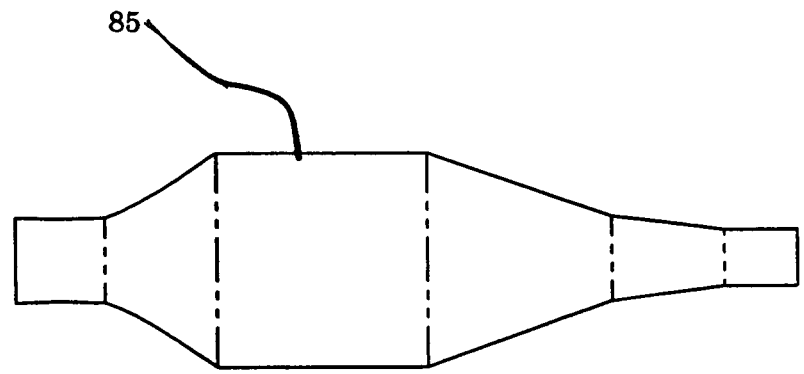
FIGS. 6A and 6B illustrate a further embodiment of the balloon that may be employed in any of the compression assemblies disclosed herein
Figure 6B:
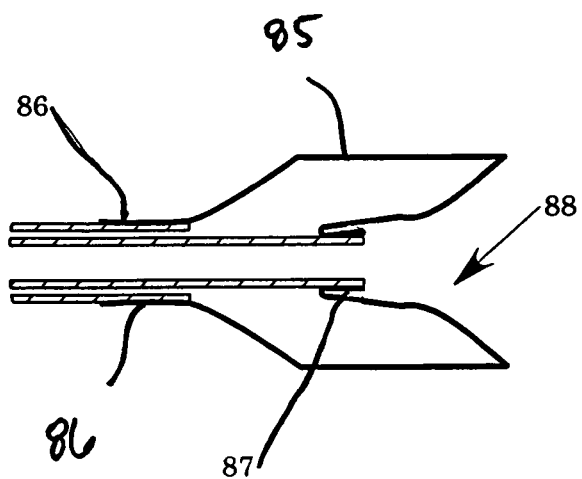

Referring now to FIG. 6A, yet another design of the compression balloon prior to attachment to the assembly is shown. Balloon 85 is folded and stacked between two attachment points 86 and 87. FIG. 6B illustrates this balloon 85 at inflation. The design and attachment of the balloon 85 may allow for the forward tissue compression. It also can form a concave distal end 88 at full inflation. The concave feature 88 of the balloon 85 may allow for more coagulant to form at the puncture site.

Figure 7A:
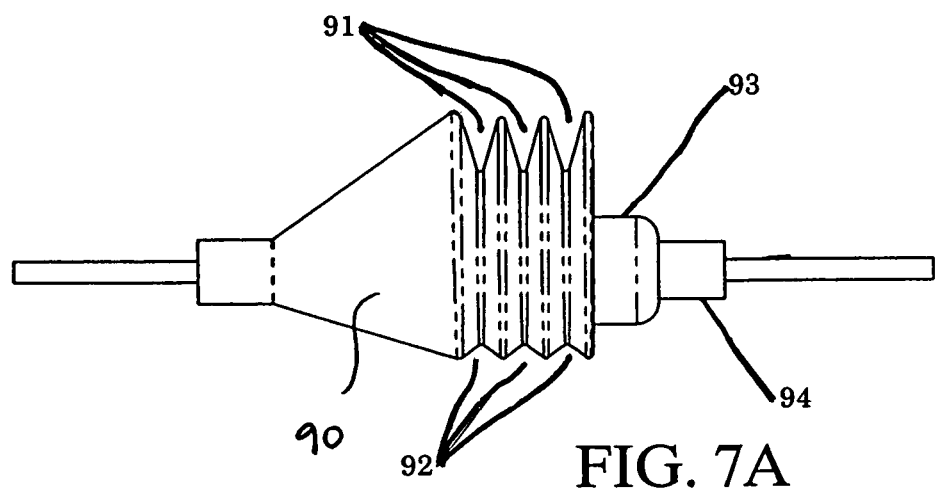
FIGS. 7A through 7C illustrate a still further embodiment of the balloon that may be employed in any of the compression assemblies disclosed herein.
Figure 7B:
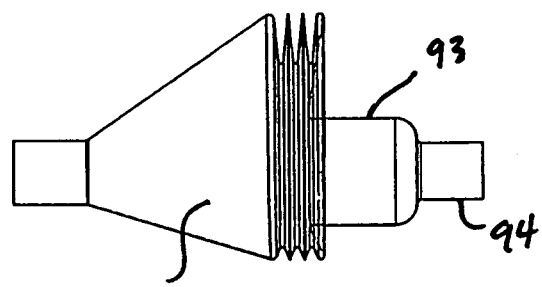
Figure 7C:
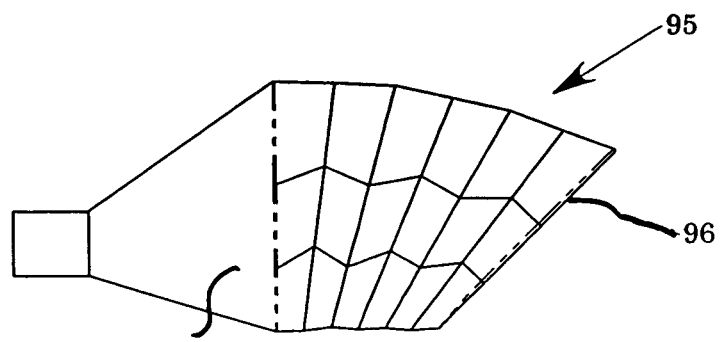

Referring now to FIG. 7A, another example of a balloon prior to attachment to the assembly is shown. Since the entry of the sheath to the vessel wall may not be perpendicular, the balloon may be molded asymmetrically. With balloon 90 at full inflation, more elongation is obtained on the top superior side relative to the bottom inferior side. This may be achieved by incorporating deeper folds 91 in the balloon material on the side with greater elongation requirements and shallower folds 92 on the opposite side. Feature 93 just proximal to the attachment point 94 may allow for the balloon elongation by folding over the attachment point 94 when the balloon is pressurized. In such a design, locating/temporary hemostasis assembly 11 may not be concentric to the compression assembly, but rather offset from the compression assembly. For example, assembly 11 may be placed closer to the inferior wall 92 of the compression balloon 90. This offset compensates for turn 95 generated during balloon 90 inflation as the result of its asymmetrical nature, and consequently centers the distal end 96 of the balloon over the puncture site at full inflation, as shown in FIG. 7C. FIG. 7B depicts this balloon design prior to inflation. It should be clear that if the molding process allows, the balloon may be designed with a distal face at an angle to the assembly shaft similar to the angle that the sheath makes with the vessel wall, to compensate for such an effect.

Figure 4B:
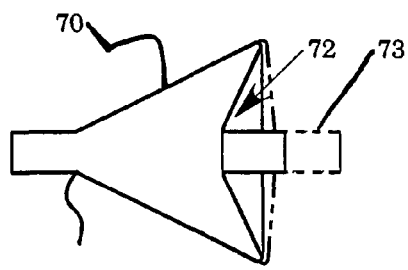

Referring back to FIG. 4B, the balloon may be designed or attached such that at full inflation, the distal face of the balloon forms a concave surface with respect to the vessel wall. In a simple conical balloon 70, this may be accomplished by attaching balloon 70 on the assembly shaft at location 72 which is proximal to point 73 where a fully inflated, unconstrained balloon may extend to. In the case of balloon with folds, such as balloons 80 and 90, this may be accomplished by making features 83 and 93 shorter than the increase in the length of the balloon as a result of inflation.

The compression balloon 55, 70, 80, 85, or 90 is generally formed of materials that can withstand elevated pressures. The balloon should be designed to withstand pressures high enough to dilate the subcutaneous tissue around the tissue track and to be able to compress the tissue against the puncture site. Polyethylene, polyethylene terephthalate, polytetrafluroethylene, nylon, polyurethane, silicone, latex, polyvinyl chloride, and thermoplastic elastomer with different durometers, are examples of such materials. These materials offer different characteristics. Some can be molded to exhibit a specific shape when inflated, and some are elastomeric. The advantage of elastomeric materials over other high pressure materials is their elongation characteristics. Therefore, elastomeric materials may have a smaller profile prior to inflation. However, they may not be pressurized as high. The compression balloon may also incorporate radio-opaque materials, so that balloon placement may be imaged and verified. It may also be desirable to deliver electrical energy, such as radio frequency energy and the like, to the puncture site to accelerate the hemostasis process. In such a case the compression balloon may be coated with electrically conductive material to provide means of delivering such energy.

It should also be noted that the compression member, thus far referred to as compression balloon, may be composed of an expansible member that is fully or partially covered by a membrane. This compression assembly when deployed can provide for the radial dilation of the surrounding tissue, as well as forward expansion resulting in tissue compression. The deployment of this expansible member may be accompanied by injection of air or fluid to assist in the expansion of the expansible member and tissue compression process. Such an embodiment is described in greater detail in co-pending U.S. patent application Ser. No. 10/718,504, assigned to the assignee of the present application and incorporated herein by reference.

Figure 8A:
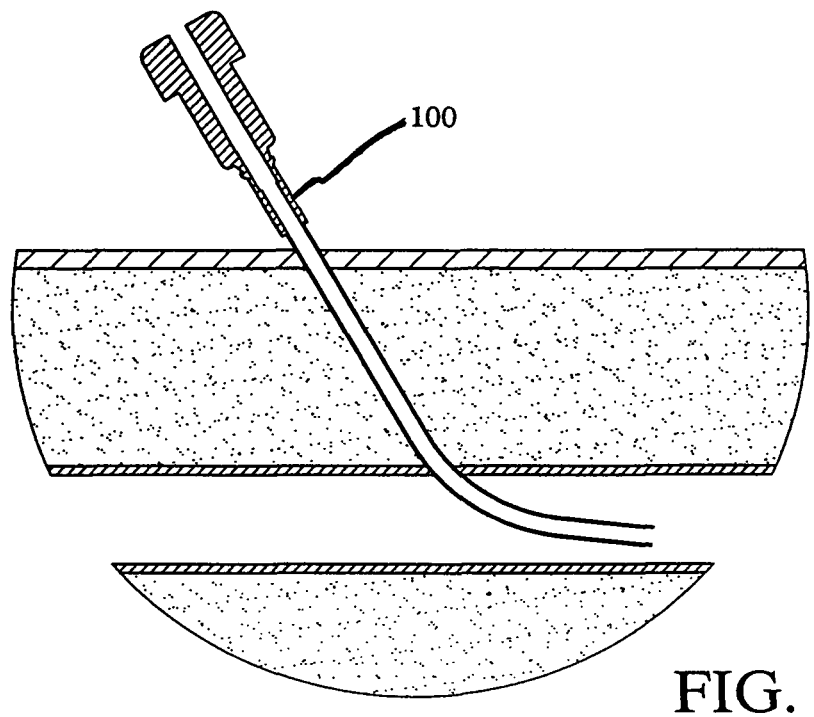
FIGS. 8A through 8G illustrate a method for hemostasis of a puncture site in a body lumen employing the system of FIG. 1D.
Figure 8B:
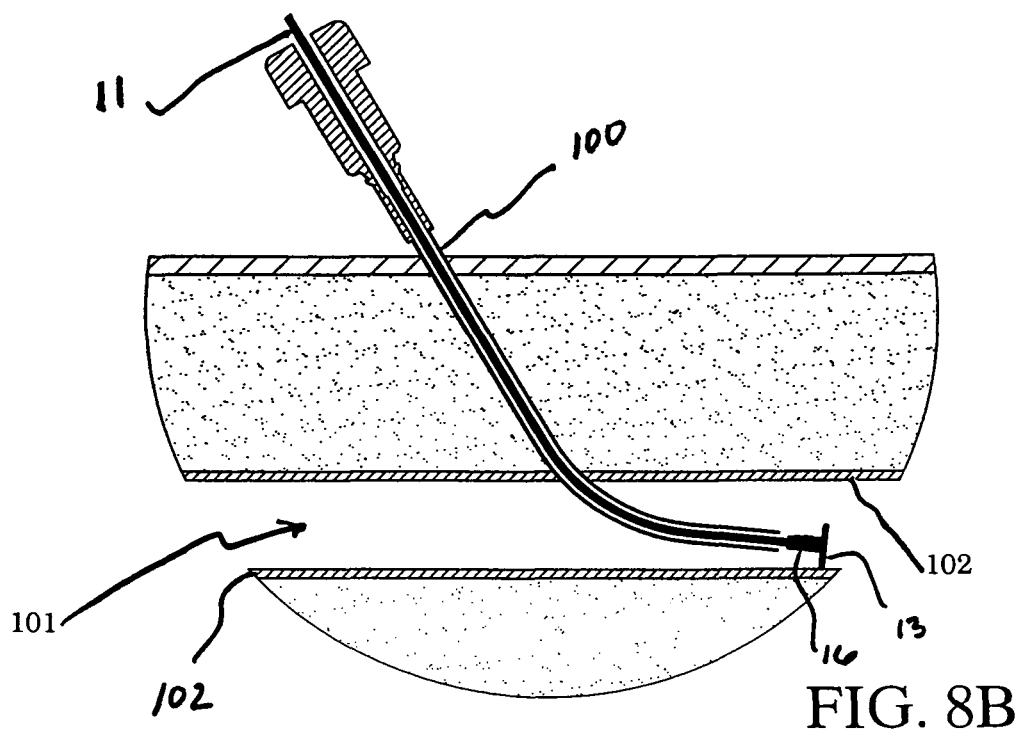
Figure 8C:
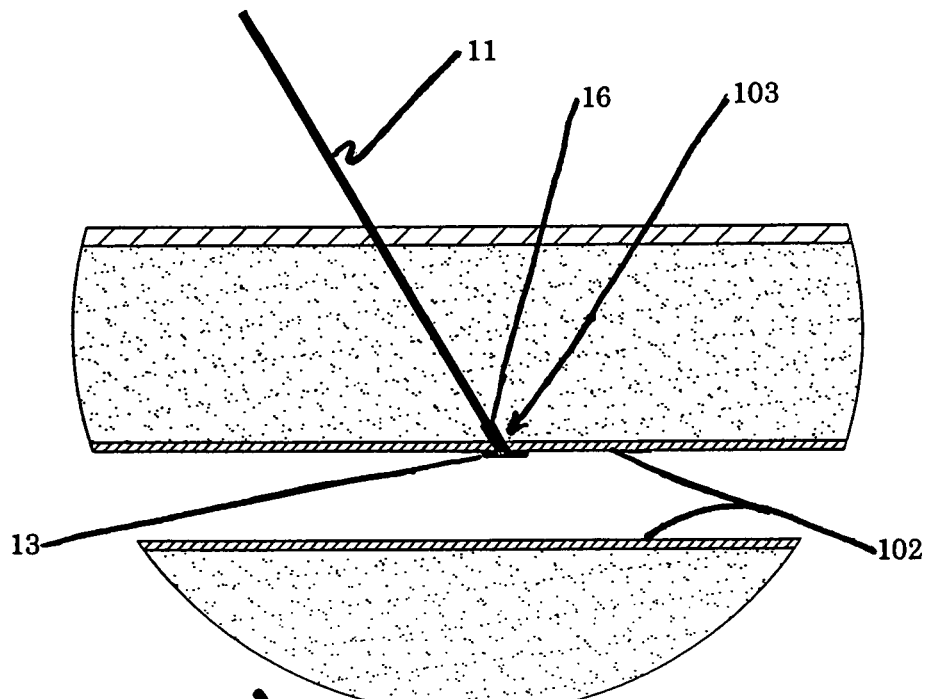

FIGS. 8A through 8G illustrate operation of closure system 10 described above with a symmetrical compression balloon 80. At the completion of a catheterization procedure, a sheath 100 remains in place as shown in FIG. 8A. Assembly 11 of the closure system 10 is slidably received within the sheath 100, as shown in FIG. 8B. Assembly 11 is fed through the sheath 100 far enough to guarantee that the distal end of the expansible member 13 is outside the sheath 100 and in the lumen 101 of blood vessel. This may be indicated by marking 19 on the outside of tubular member 12. Once in place, the expansible member 13 is deployed by pushing the deployment handle 14 forwardly, as in the case of a push type locating mechanism (FIGS. 2A and 2B). Locating assembly 11 is then pulled back until expansible member 13 is placed against the distal tip of the sheath 100. This would be indicated as resistance is felt when assembly 11 is pulled back. The sheath 100 is then slowly removed from the body, and over assembly 11, and discarded. As shown in FIG. 8C, assembly 11 would be left behind with locating member 13 against vessel wall 102 at the puncture site 103, inside the vessel, and temporary hemostasis plug 16 remains lodged in the vessel wall at 103, preventing blood from leaking out.

Figure 8D:
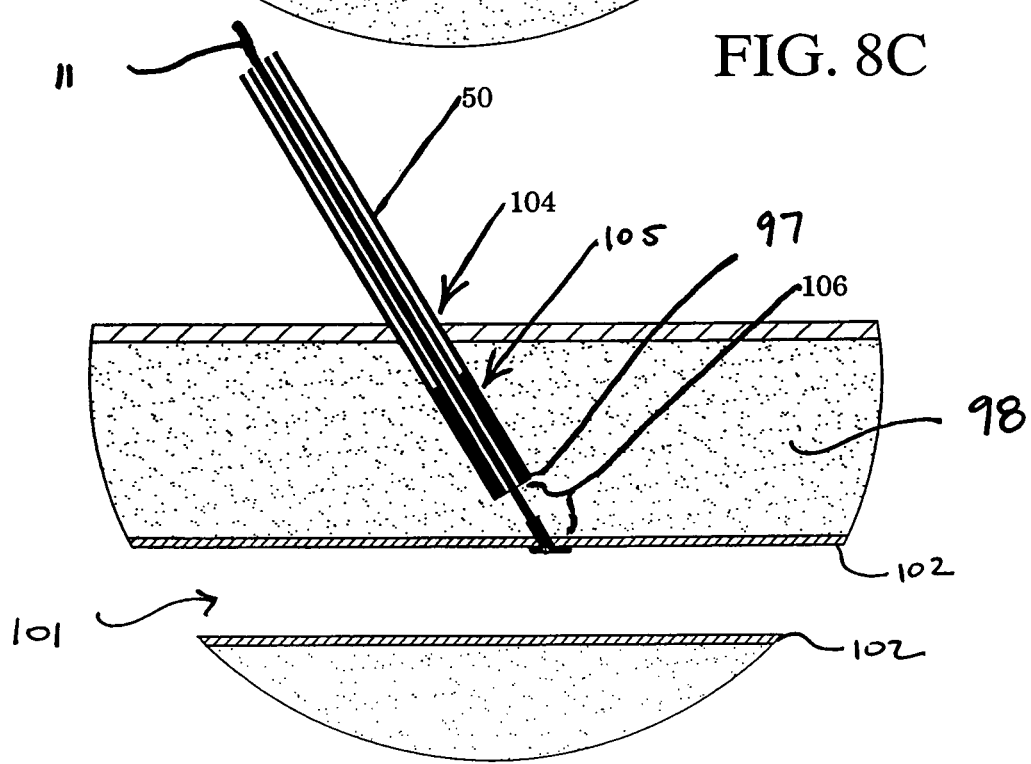
Figure 8E:
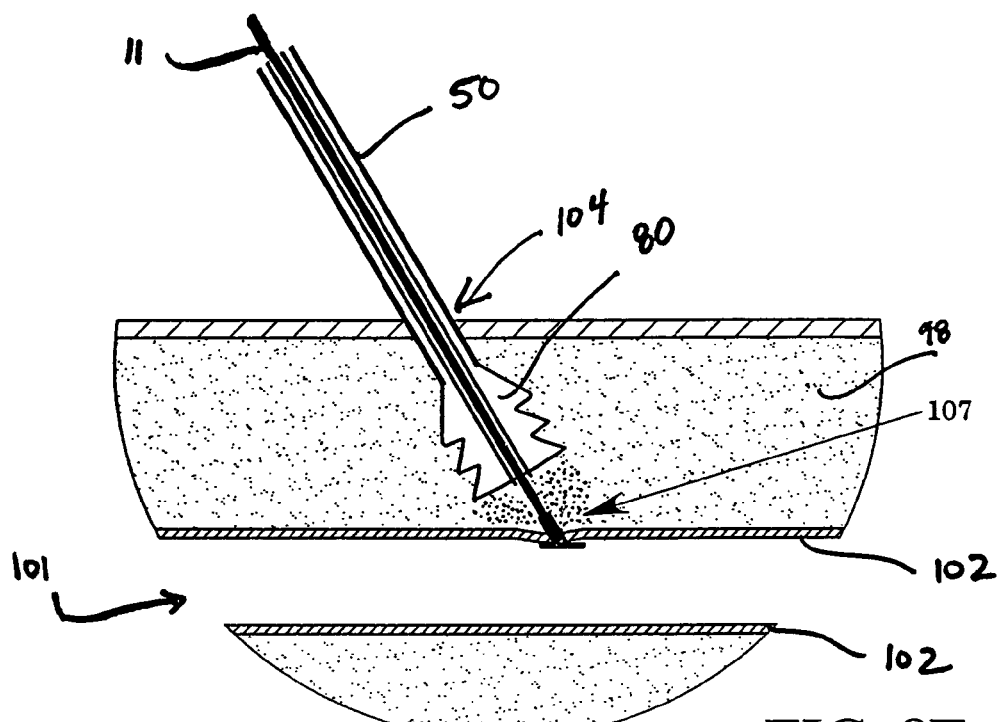
Figure 8F:
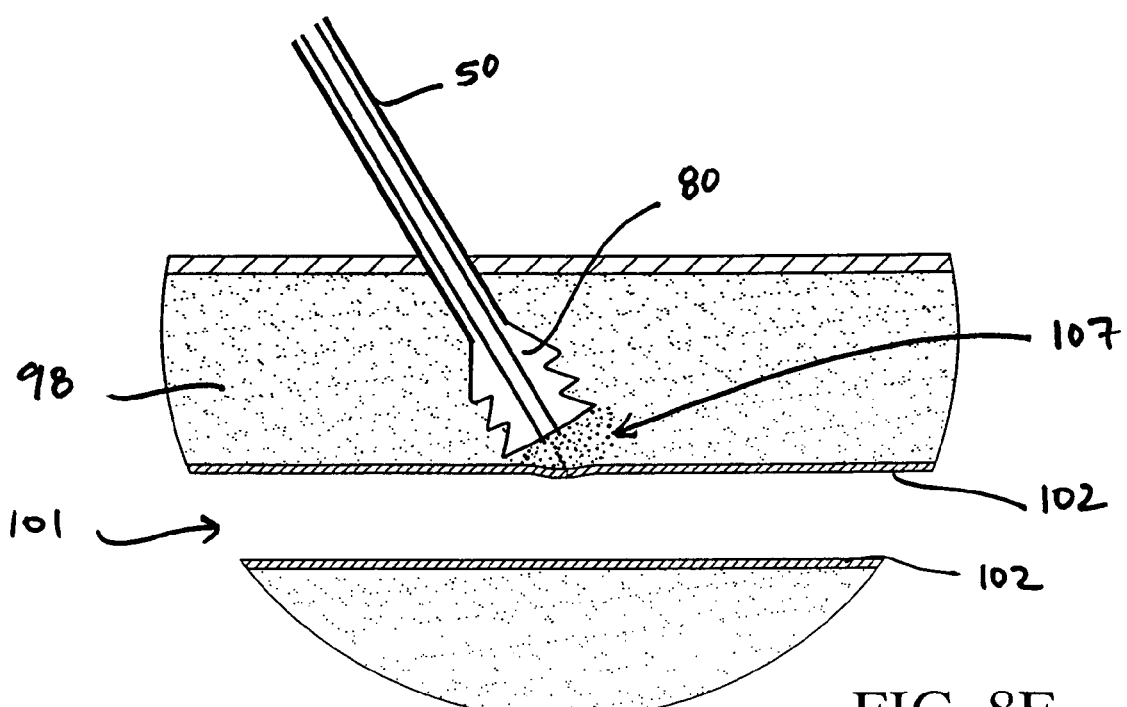

Referring now to FIG. 8D, the proximal end of assembly 11 is then pushed through the distal end of compression assembly 50 and fed through the lumen of its tubular member 51 until it penetrates seal 52, and exits the proximal end of assembly 50. Compression assembly 50 is then guided over tubular member 12 of locating/temporary hemostasis assembly 11 through an opening in skin 104, through tissue tract 105, until its distal end 97 is placed at a predetermined distance 106 from the vessel wall 102 and against subcutaneous tissue 98. This positioning may be indicated by marking 18 on tubular member 12. The compression balloon is then inflated to its optimum pressure so as to provide targeted micro compression, as shown in FIG. 8E. Tissue compression 107 over the puncture site 103 of the vessel wall 102 can now provide the means for hemostasis. Assembly 11 of the closure device is then contracted and removed from the body through the lumen of the compression assembly 50, as shown in FIG. 8F.

Figure 8G:
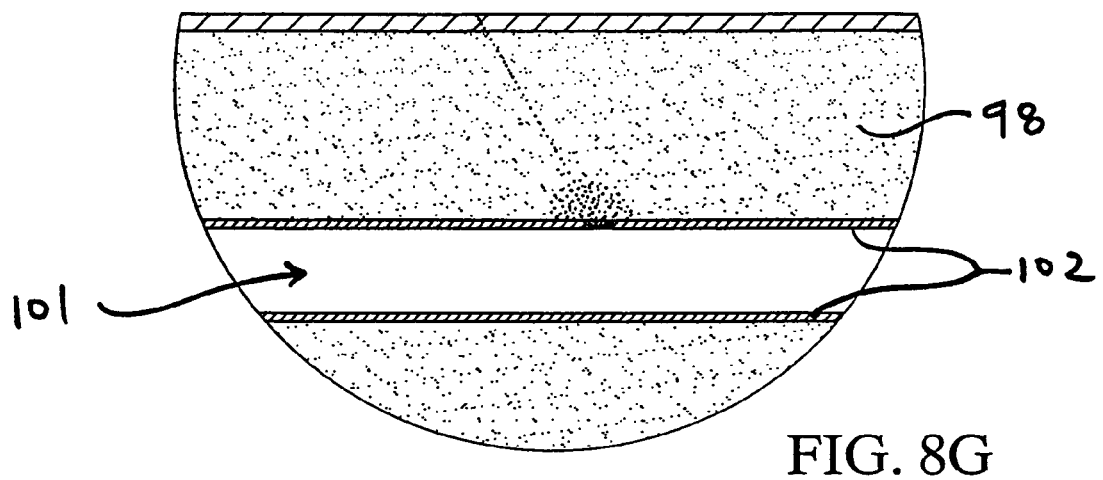

The compression assembly 50 may remain in the body as long as necessary to allow the body's own natural wound healing mechanism to achieve hemostasis. The balloon 80 is then deflated, and the compression assembly 50 is removed, as shown in FIG. 8G.

Figure 9A:
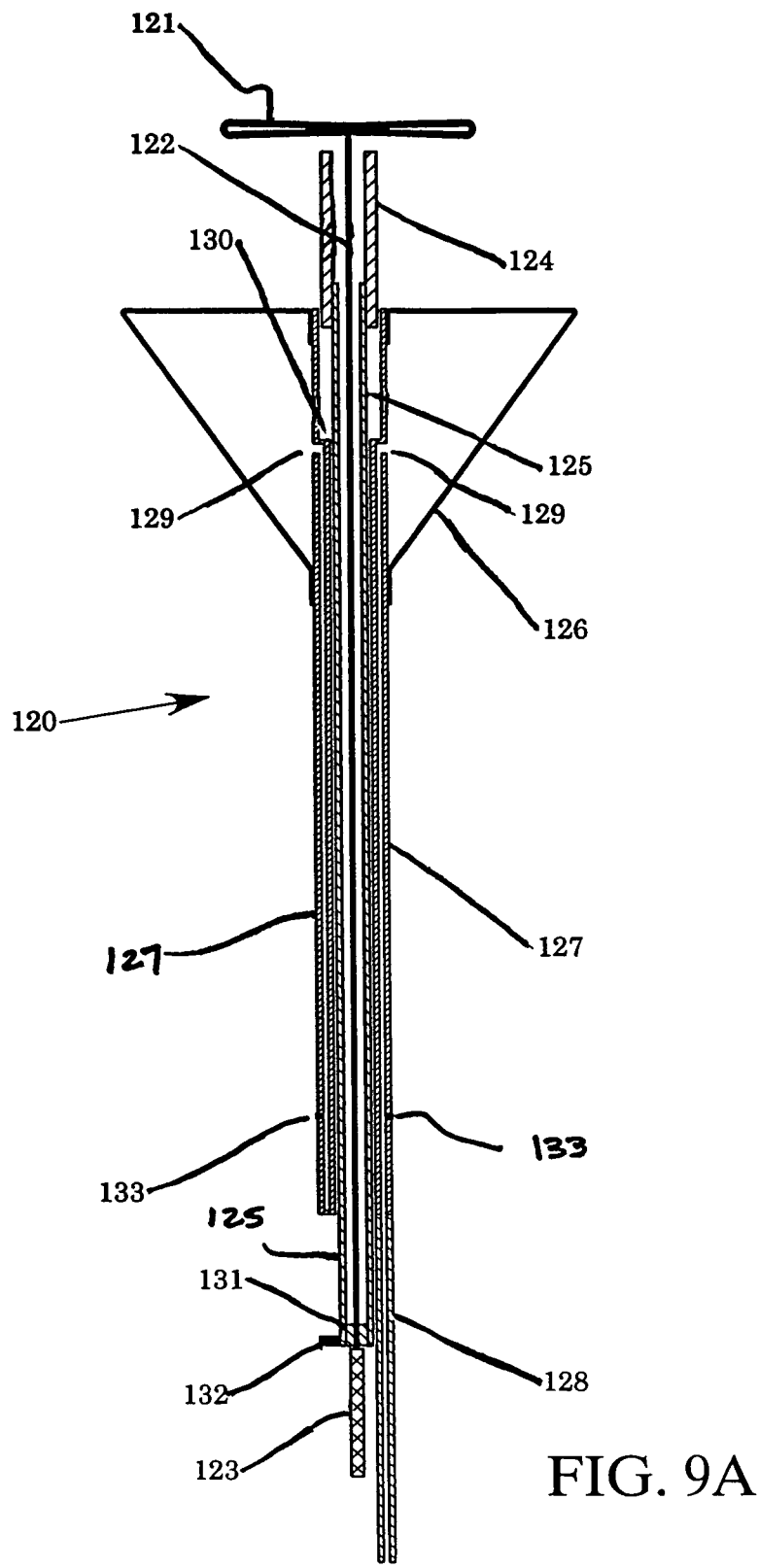
FIGS. 9A through 9C illustrate another system embodiment for hemostasis of a puncture site in a body lumen constructed in accordance with the principles of the present invention.
Figure 9B:
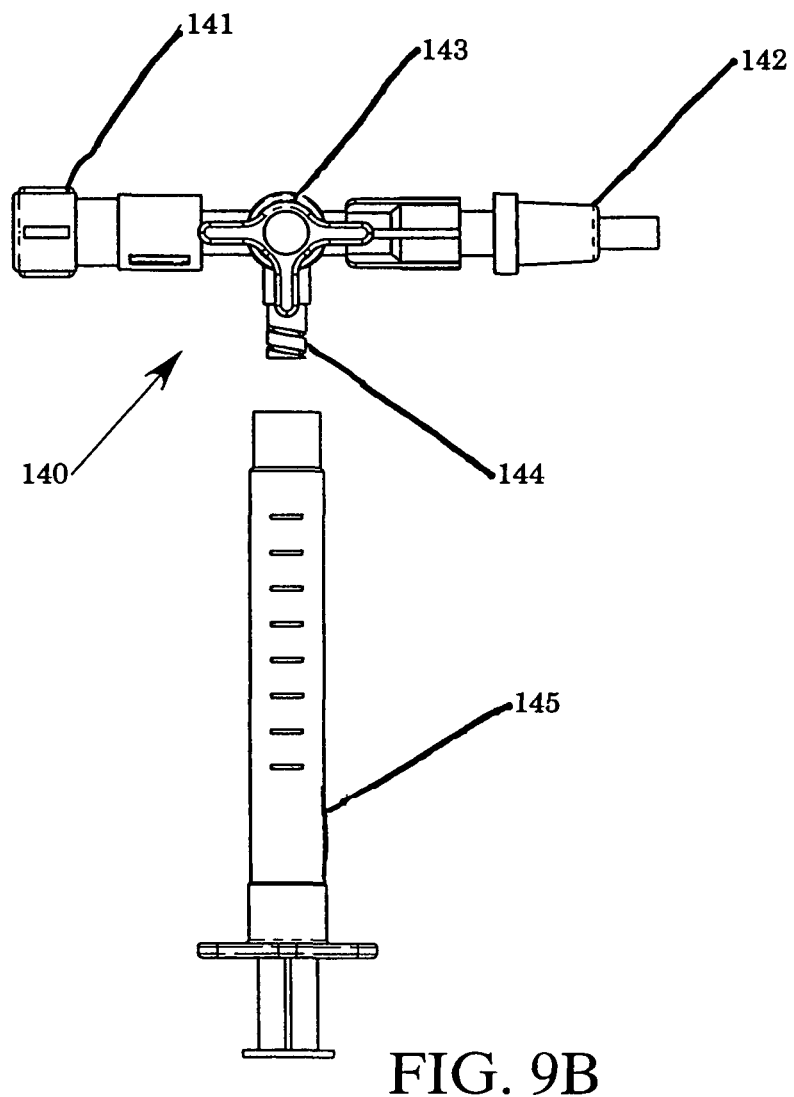
Figure 9C:
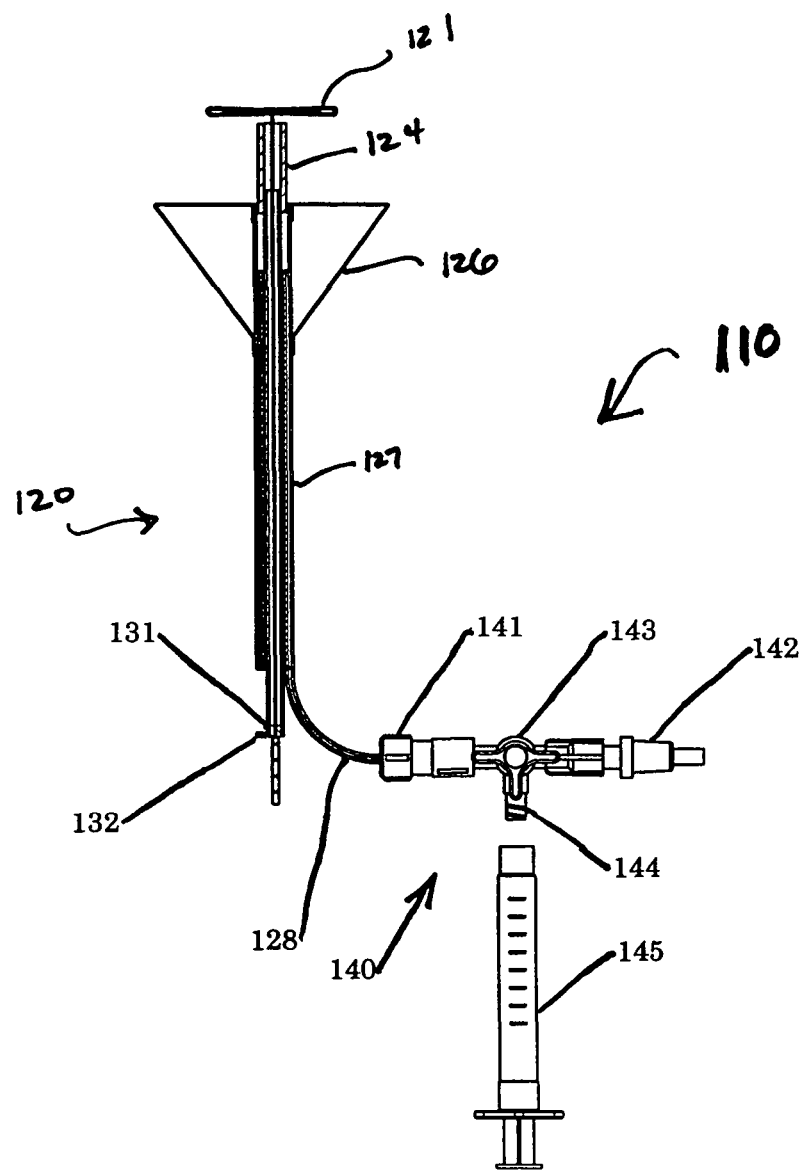

FIGS. 9A through 9C illustrate another system 110 embodiment for hemostasis of a puncture site in a body lumen constructed in accordance with the principles of the present invention. The system 110 comprises a catheter assembly 120 and an inflation assembly 140. Catheter assembly 120 has a cross-sectional profile smaller than the sheath 100. FIG. 9A shows the catheter assembly 120 which comprises a locating/temporary hemostasis mechanism 121, 124 (and means for deployment) integrated with a compression balloon 126 and a second tubular member 127 for inflating the compression balloon 126. The catheter assembly 120 includes locating expansible member 121 and means for its deployment and retraction, namely push/pull member 122 and handle assembly 123. Member 122 exits a proximal end of the first tubular member 125 through seal 131. Since first tubular member 125 is in communication with blood, seal 131 prevents blood from flowing out. The movement of handle assembly 123 may be limited by the proximal end of the first tubular member 125 and by interference of expansible member 121 with a distal end of tubular member 125. Movement of plug member 124 and tubular member 125 may be limited by interference of feature 132 with a proximal end of second tubular member 127 and by interference of plug 124 with a distal end of tubular member 127 at feature 130.

It may be desirable in some embodiments to allow the expansible member 121 and the hemostasis plug 124 to move freely forward in a distal direction when the compression balloon 126 is inflated. Therefore an intermediate position for the relative position of tubular members 125 and 127 may be established before feature 132 interferes with the proximal end of tubular member 127. In this position the expansible member 121 and the hemostasis plug 124 are deployed and the compression balloon 126 is placed at the desired distance to the vessel wall 102. This intermediate position may be identifiable by a visual mark or by a mechanical detent as described above. It may also be desirable to design the deployment and contraction mechanism 122 of the expansible member 121 and the temporary hemostasis plug 124 so that the temporary hemostasis plug 124 is deployed first followed by the locating mechanism 121. When contracting these members, the locating member 121 is retracted within the hemostasis plug 124 first and then the plug 124 is retracted into second tubular member 127.

Temporary hemostasis plug 124 is at the distal end of the first flexible elongated tubular member 125. Compression balloon 126 is attached at the distal end of the second flexible tubular member 127. Second tubular member 127 terminates in flexible inflation tube 128. Second tubular member 127 is in fluid communication with compression balloon 126 through ports 129. The two tubular members 125 and 127 may be moveable respect to each other, as shown in FIG. 9A. Expansible member 121 and temporary hemostasis plug 124 may be retracted and housed inside the second tubular member 127 at feature 130 after the compression balloon 126 has been inflated. System 110 may also be designed to have the two tubular members 125 and 127 be fixed relative to each other. In such a case, the inflation process and distal expansion of compression balloon 126 may cause members 121 and 124 to be retracted and removed from the vessel lumen 101 and the vessel wall 102. FIG. 9B shows inflation assembly 140 which generally comprises a quick connect 141 that connects inflation mechanism 140 to inflation tube 128 of catheter assembly 120, a pressure relief valve 142, a stopcock 143, and a luer lock 144 for attaching syringe 145.

Operation of system 110 with the sheath 100 still in place involves positioning catheter assembly 120 through the sheath 100, until a tip of the catheter assembly 120 is outside of the sheath 100 and is in the vessel lumen 101. As shown in FIG. 9A, this may be indicated by mark 133 on the second tubular member 127. The first tubular member 125 is moved forward to expose plug 124. Handle assembly 123 is then moved forward to deploy the expansible member 121. Catheter assembly 120 is then pulled back until resistance is felt, indicating that expansible member 121 is at the distal end of the sheath 100. The sheath is then pulled back, and slowly removed from the body, over the entire length of the catheter 120, leaving expansible member 121 against the inside of the vessel wall 102, and with hemostasis plug 124 lodged in the puncture site 103 in the vessel wall 102. The sheath 100 can be discarded. The compression balloon 126 is now located and fixed at a predetermined distance 106 from the vessel wall 102.

Inflation assembly 140 is then connected to inflation tube 128 via quick connect 141 as illustrated in FIG. 9C. Syringe 145 containing air, saline, other agents (e.g., clot promoting solutions), or a combination thereof is connected to luer lock 144. With stopcock 143 in inflation/deflation position the balloon 126 is inflated to the desired inflation pressure, causing radial and axial expansion of the balloon 126 and causing subcutaneous tissue compression 107 against the puncture site 103, overcoming the blood pressure and producing hemostasis. The inflation process is complete when air or fluid starts to exit from the pressure relief valve 142. Stopcock 143 is turned to hold position allowing the pressure to be maintained inside compression balloon 126. Handle assembly 123 is then manipulated to sequentially retract the locating member 121 first and then the temporary hemostasis plug 124. The compression balloon 126 is allowed to remain inflated for a period of time against the subcutaneous tissue 98. Once the desired period of compression time is elapsed, stopcock 143 is put in the inflation/deflation position. The syringe 145 can be used to facilitate removal of the medium from the compression balloon 126 and furthermore collapse the balloon 126 around the tubular member 127. Catheter assembly 120 is then removed from the body.

Figure 10:
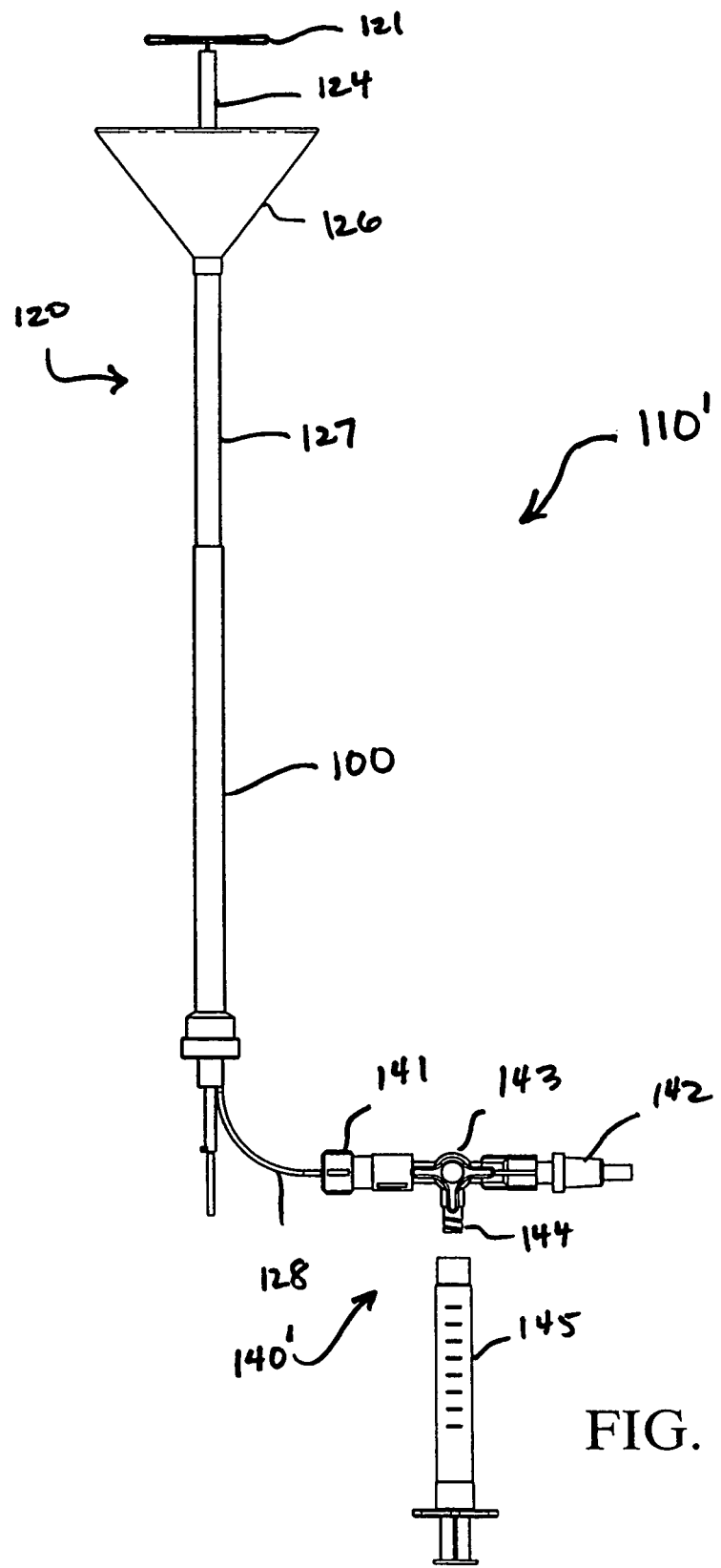
FIG. 10 illustrates yet another system embodiment for hemostasis of a puncture site in a body lumen constructed in accordance with the principles of the present invention.

FIG. 10 illustrates yet another system 110' embodiment for hemostasis of a puncture site in a body lumen constructed in accordance with the principles of the present invention. This is an integrated, unitary structure 120, containing all the working elements as discussed above with reference to FIGS. 9A through 9C. In this embodiment, the inflation assembly 140' of system 110' has a profile that is substantially greater than the sheath 100. As such, the second flexible elongated tubular member 127 is made of sufficient length to allow for complete removal of the sheath 100 from the body when the locating expansible member 121 and temporary hemostasis plug 124 are deployed. The sheath 100 stays with the assembly 120 until hemostasis is achieved and the system 110' is removed.

Figures 11A, 11B, 11C:
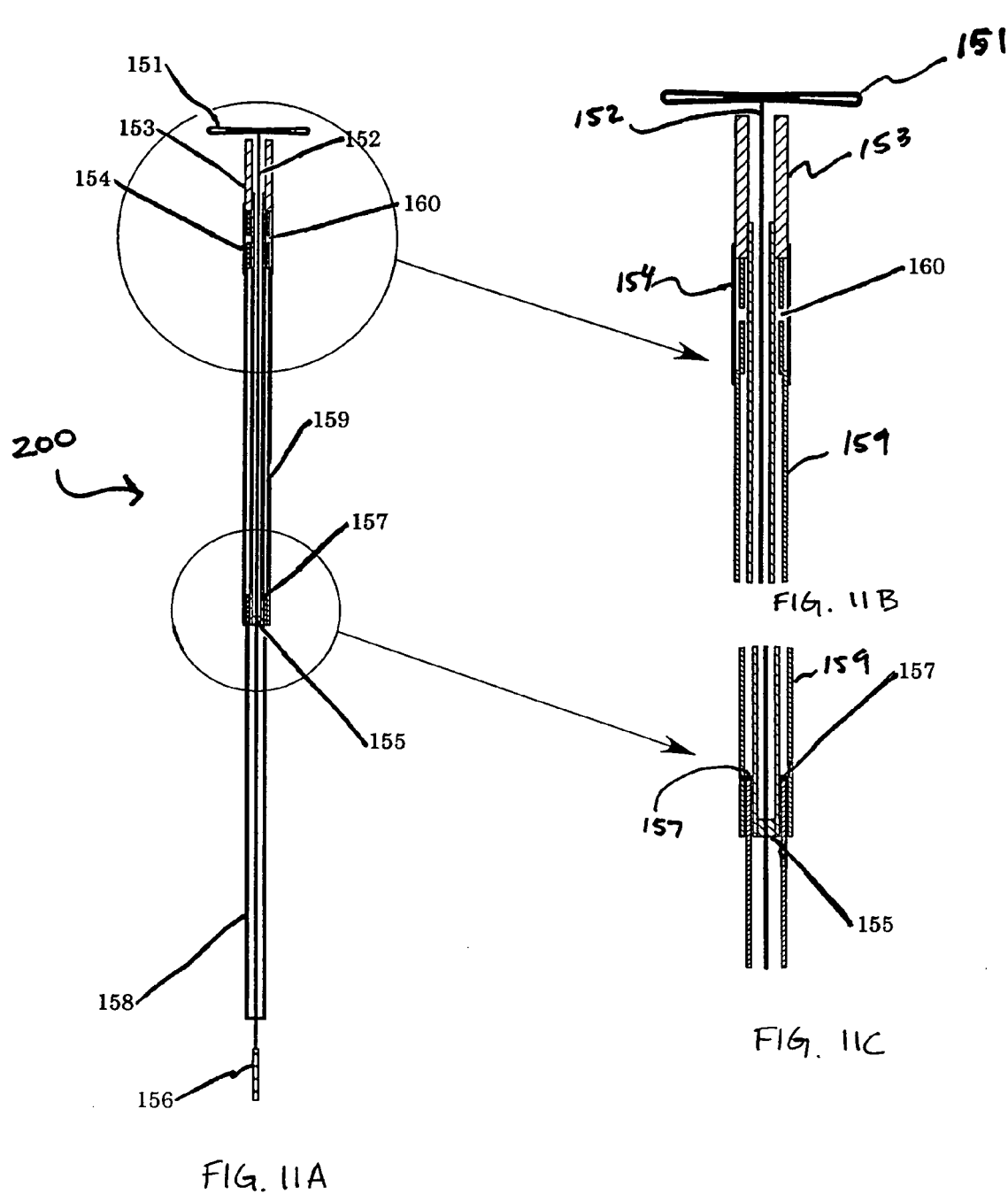
FIGS. 11A through 11C illustrate a further system embodiment for hemostasis of a puncture site in a body lumen constructed in accordance with the principles of the present invention.

FIGS. 11A through 11C illustrate yet another system 200 embodiment for hemostasis of a puncture site in a body lumen constructed in accordance with the principles of the present invention. This is also an integrated structure, including several of the working elements discussed above with reference to FIGS. 9A through 9C. For example, the functions of locating expansible member 151, push/pull member 152, temporary hemostasis plug 153, compression balloon 154, seal 155, and handle assembly 156 are similar to those described above. As depicted in FIG. 11C, the pumping mechanism includes a compression seal 157 and a pump handle 158. The pump assembly 157, 158 compresses the air in piston 159 to inflate compression balloon 154. Balloon 154 is in fluid communication with 159 through opening 160, as depicted in FIG. 11B. System 200 has a cross-sectional profile that is smaller than the inside diameter of the sheath 100 being used. Therefore the sheath 100 can completely slide off over the system 200 when the locating expansible member 151 and temporary hemostasis plug 153 have been deployed and are placed in the vessel appropriately.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A method for hemostasis of a puncture site in a wall of a blood vessel at an end of a tissue tract having a sheath therein, the method comprising:

providing a locating member having a proximal end, a distal end, and an expansible member disposed on the distal end thereof, inserting the locating member through the sheath in the tissue tract so that the expansible member on the locating member enters a lumen of the blood vessel;

expanding the expansible member on the inserted locating member and drawing the inserted locating member proximally so that the expanded expansible member covers the puncture site in the vessel wall;

removing the sheath from the tissue tract while the inserted locating member remains in place;

providing a tubular compression member having a proximal end, a distal end, a central passage between said proximal end and said distal end, and an expansible tissue compression element disposed over the distal portion thereof, and advancing the tubular compression member over the inserted locating member after the sheath has been removed from the tissue tract so that the locating member is received in the central passage of the tubular compression member and a distal end of the expansible tissue compression element is located within the tissue tract at a predetermined distance proximal from the wall of the blood vessel to define a tissue compression region; and expanding the expansible tissue compression element within the tissue tract above the blood vessel wall to apply pressure against subcutaneous tissue and to compress said tissue over the puncture site in the blood vessel wall to promote hemostasis, wherein the compression element is not in direct contact with the vessel wall, and wherein the expansible tissue compression element on the compression member is left in place until hemostasis has been achieved.

2. The method of claim 1, wherein the predetermined distance is in a range from about 0.05 inch to about 0.5 inch.

3. The method of claim 2, wherein the predetermined distance is in a range from about 0.2 inch to about 0.3 inch.

4. The method of claim 1, wherein the expansible tissue compression element on the compression member comprises a balloon.

5. The method of claim 4, wherein expanding comprises inflating a superior aspect of the balloon greater than an inferior aspect of the balloon.

6. The method of claim 4, wherein expanding comprises inflating a distal face of the balloon at an angle to the compression member similar to an angle formed between the compression member and the blood vessel.

7. The method of claim 4, wherein expanding comprises inflating the balloon to a deployed configuration comprising a conical shape.

8. The method of claim 4, wherein expanding comprises unfolding concentric folds of the balloon.

9. The method of claim 4, wherein expanding comprises inflating the balloon to a deployed configuration having a concave distal end.

10. The method of claim 1, wherein the expansible member on the locating member is expanded to an expanded configuration within the blood vessel having a diameter in a range from about 0.05 inch to about 0.5 inch.

11. The method of claim 1, further comprising contracting and withdrawing the locating member while the compression member remains in place.

12. The method of claim 1, further comprising imaging the expansible element during positioning.

13. The method of claim 1, further comprising delivering radio frequency energy, ultrasound energy, or microwave energy to the puncture site.

14. The method of claim 1, further comprising delivering a clot promoting agent or anti-infection agent to the puncture site.

* * * * *